(12) United States Patent
Hartwell

(10) Patent No.: US 9,220,822 B2
(45) Date of Patent: *Dec. 29, 2015

(54) WOUND DRESSING

(71) Applicant: Smith & Nephew PLC, London (GB)

(72) Inventor: Edward Yerbury Hartwell, Hull (GB)

(73) Assignee: Smith & Nephew PLC, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/276,983

(22) Filed: May 13, 2014

(65) Prior Publication Data

US 2014/0249493 A1 Sep. 4, 2014

Related U.S. Application Data

(63) Continuation of application No. 12/744,218, filed as application No. PCT/GB2008/051089 on Nov. 20, 2008, now Pat. No. 8,808,274.

(30) Foreign Application Priority Data

Nov. 21, 2007 (GB) .................................... 0722820.8
Sep. 17, 2008 (GB) .................................... 0817040.9

(51) Int. Cl.
*A61M 1/00* (2006.01)
*A61F 13/02* (2006.01)
(Continued)

(52) U.S. Cl.
CPC ........ *A61M 1/0023* (2013.01); *A61F 13/00063* (2013.01); *A61F 13/00068* (2013.01); *A61F 13/02* (2013.01); *A61F 13/0216* (2013.01); *A61M 1/00* (2013.01); *A61M 1/009* (2014.02); *A61M 1/0049* (2013.01); *A61M 1/0088* (2013.01); *A61M 1/0092* (2013.01); *A61M 27/00* (2013.01); *A61F 13/00029* (2013.01); *A61F 13/00046* (2013.01);
(Continued)

(58) Field of Classification Search
CPC ................ A61F 13/02; A61F 13/0216; A61F 13/00029; A61F 13/00046; A61F 13/00068; A61F 2013/00536; A61M 1/00; A61M 1/0049; A61M 1/0088; A61M 1/009; A61M 27/00; A61M 2205/7527; A61M 2205/7536
See application file for complete search history.

(56) References Cited

U.S. PATENT DOCUMENTS

| 695,270 A | 3/1902 | Beringer |
|---|---|---|
| 1,480,562 A | 1/1924 | Mock |

(Continued)

FOREIGN PATENT DOCUMENTS

| CN | 2186074 | 12/1994 |
|---|---|---|
| DE | 847475 | 8/1952 |

(Continued)

OTHER PUBLICATIONS

US 6,216,701, 04/2001, Heaton et al. (withdrawn).
(Continued)

*Primary Examiner* — Philip R Wiest
*Assistant Examiner* — Benjamin Klein
(74) *Attorney, Agent, or Firm* — Knobbe, Martens, Olson & Bear, LLP

(57) ABSTRACT

A method and apparatus are disclosed for dressing a wound. The apparatus comprises a sealing layer comprising at least one orifice, an absorbent layer over the sealing layer, absorbing wound exude and a liquid impermeable, gas permeable filter layer over the absorbent layer.

20 Claims, 3 Drawing Sheets

(51) Int. Cl.
*A61M 27/00* (2006.01)
*A61F 13/00* (2006.01)

(52) U.S. Cl.
CPC ............... *A61F 2013/00536* (2013.01); *A61M 2205/7527* (2013.01); *A61M 2205/7536* (2013.01)

(56) References Cited

U.S. PATENT DOCUMENTS

| | | |
|---|---|---|
| 2,280,915 A | 4/1942 | Johnson |
| 2,367,690 A | 7/1943 | Purdy |
| 2,568,933 A | 9/1951 | Robbins |
| 2,632,443 A | 3/1953 | Lesher |
| 2,682,873 A | 7/1954 | Evans et al. |
| 2,910,763 A | 8/1955 | Lauterbach |
| 3,115,138 A | 12/1963 | McElvenny et al. |
| 3,367,332 A | 2/1968 | Groves |
| 3,572,340 A | 3/1971 | Lloyd et al. |
| 3,874,387 A | 4/1975 | Barbieri |
| 3,993,080 A | 11/1976 | Loseff |
| RE29,319 E | 7/1977 | Nordby et al. |
| 4,102,342 A | 7/1978 | Akiyama et al. |
| 4,112,947 A | 9/1978 | Nehring |
| 4,136,696 A | 1/1979 | Nehring |
| 4,184,510 A | 1/1980 | Murry et al. |
| 4,217,894 A | 8/1980 | Franetzki |
| 4,219,019 A | 8/1980 | Coates |
| 4,224,945 A | 9/1980 | Cohen |
| 4,316,466 A | 2/1982 | Babb |
| 4,382,441 A | 5/1983 | Svedman |
| 4,398,910 A | 8/1983 | Blake et al. |
| 4,465,485 A | 8/1984 | Kashmer et al. |
| 4,534,356 A | 8/1985 | Papadakis |
| 4,573,965 A | 3/1986 | Russo |
| 4,608,041 A | 8/1986 | Nielsen |
| 4,655,754 A | 4/1987 | Richmond et al. |
| 4,655,766 A | 4/1987 | Theeuwes et al. |
| 4,681,562 A | 7/1987 | Beck et al. |
| 4,710,165 A | 12/1987 | McNeil et al. |
| 4,778,446 A | 10/1988 | Jensen |
| 4,792,328 A | 12/1988 | Beck et al. |
| 4,826,494 A | 5/1989 | Richmond et al. |
| 4,828,546 A | 5/1989 | McNeil et al. |
| 4,921,488 A | 5/1990 | Maitz et al. |
| 4,936,834 A | 6/1990 | Beck et al. |
| 4,969,880 A | 11/1990 | Zamierowski |
| 4,972,829 A | 11/1990 | Knerr |
| 4,994,022 A | 2/1991 | Steffler et al. |
| 5,055,198 A | 10/1991 | Shettigar |
| 5,056,510 A | 10/1991 | Gilman |
| 5,073,172 A | 12/1991 | Fell |
| 5,100,396 A | 3/1992 | Zamierowski |
| 5,134,994 A | 8/1992 | Say |
| 5,152,757 A | 10/1992 | Eriksson |
| 5,167,613 A | 12/1992 | Karami et al. |
| 5,176,663 A | 1/1993 | Svedman et al. |
| 5,215,519 A | 6/1993 | Shettigar |
| 5,234,419 A | 8/1993 | Bryant et al. |
| 5,261,893 A | 11/1993 | Zamierowski |
| 5,266,928 A | 11/1993 | Johnson |
| 5,279,608 A | 1/1994 | Cherif Cheikh |
| 5,328,614 A | 7/1994 | Matsumura |
| 5,358,494 A | 10/1994 | Svedman |
| 5,380,280 A | 1/1995 | Peterson |
| 5,437,651 A | 8/1995 | Todd et al. |
| 5,445,604 A | 8/1995 | Lang |
| 5,489,280 A | 2/1996 | Russell |
| 5,498,338 A | 3/1996 | Kruger et al. |
| 5,527,293 A | 6/1996 | Zamierowski |
| 5,536,233 A | 7/1996 | Khouri |
| 5,549,584 A * | 8/1996 | Gross .................. 604/313 |
| 5,624,423 A | 4/1997 | Anjur et al. |
| 5,636,643 A | 6/1997 | Argenta et al. |
| 5,643,189 A | 7/1997 | Masini |
| 5,645,081 A | 7/1997 | Argenta et al. |
| 5,662,583 A | 9/1997 | Khouri |
| 5,676,634 A | 10/1997 | Khouri |
| 5,678,564 A | 10/1997 | Lawrence et al. |
| 5,695,445 A | 12/1997 | Khouri |
| 5,701,917 A | 12/1997 | Khouri |
| 5,733,337 A | 3/1998 | Carr et al. |
| 5,759,570 A | 6/1998 | Arnold |
| 5,776,098 A | 7/1998 | Silver et al. |
| 5,785,688 A | 7/1998 | Joshi et al. |
| 5,817,145 A | 10/1998 | Augustine et al. |
| 5,830,496 A | 11/1998 | Freeman |
| 5,833,646 A | 11/1998 | Masini |
| 5,843,011 A | 12/1998 | Lucas |
| 5,868,933 A | 2/1999 | Patrick et al. |
| 5,876,611 A | 3/1999 | Shettigar |
| 5,964,723 A | 10/1999 | Augustine |
| 6,010,527 A | 1/2000 | Augustine et al. |
| 6,013,097 A | 1/2000 | Augustine et al. |
| 6,071,267 A | 6/2000 | Zamierowski |
| 6,093,160 A | 7/2000 | Augustine et al. |
| 6,103,951 A | 8/2000 | Freeman |
| 6,110,197 A | 8/2000 | Augustine et al. |
| 6,117,111 A | 9/2000 | Fleischmann |
| 6,135,116 A | 10/2000 | Vogel et al. |
| 6,142,982 A | 11/2000 | Hunt et al. |
| 6,168,800 B1 | 1/2001 | Dobos et al. |
| 6,176,307 B1 | 1/2001 | Danos et al. |
| 6,225,523 B1 | 5/2001 | Masini |
| 6,248,084 B1 | 6/2001 | Augustine et al. |
| 6,254,567 B1 | 7/2001 | Treu et al. |
| 6,255,552 B1 | 7/2001 | Cummings et al. |
| 6,257,847 B1 | 7/2001 | Silver et al. |
| 6,261,283 B1 | 7/2001 | Morgan et al. |
| 6,267,740 B1 | 7/2001 | Augustine et al. |
| 6,287,521 B1 | 9/2001 | Quay et al. |
| 6,291,050 B1 | 9/2001 | Cree et al. |
| 6,293,917 B1 | 9/2001 | Augustine et al. |
| 6,345,623 B1 | 2/2002 | Heaton et al. |
| 6,398,767 B1 | 6/2002 | Fleischmann |
| 6,402,724 B1 | 6/2002 | Smith et al. |
| 6,440,167 B2 | 8/2002 | Shimizu |
| 6,450,773 B1 | 9/2002 | Upton |
| 6,458,109 B1 | 10/2002 | Henley et al. |
| 6,465,708 B1 | 10/2002 | Augustine |
| 6,468,295 B2 | 10/2002 | Augustine et al. |
| 6,471,685 B1 | 10/2002 | Johnson |
| 6,471,982 B1 | 10/2002 | Lydon et al. |
| 6,481,986 B1 | 11/2002 | Silver et al. |
| 6,491,684 B1 | 12/2002 | Joshi et al. |
| 6,500,112 B1 | 12/2002 | Khouri |
| 6,547,756 B1 | 4/2003 | Greter et al. |
| 6,553,998 B2 | 4/2003 | Heaton et al. |
| 6,580,012 B1 | 6/2003 | Augustine et al. |
| 6,599,262 B1 | 7/2003 | Masini |
| 6,626,891 B2 | 9/2003 | Ohmstede |
| 6,638,270 B2 | 10/2003 | Johnson |
| 6,648,862 B2 | 11/2003 | Watson |
| 6,673,028 B1 | 1/2004 | Argenta et al. |
| 6,676,610 B2 | 1/2004 | Morton et al. |
| 6,676,631 B1 | 1/2004 | Greter |
| 6,685,681 B2 | 2/2004 | Lockwood et al. |
| 6,695,823 B1 | 2/2004 | Lina et al. |
| 6,695,824 B2 | 2/2004 | Howard et al. |
| 6,699,213 B1 | 3/2004 | Annis et al. |
| 6,752,794 B2 | 6/2004 | Lockwood et al. |
| 6,755,807 B2 | 6/2004 | Risk et al. |
| 6,764,462 B2 | 7/2004 | Risk, Jr. et al. |
| 6,767,334 B1 | 7/2004 | Randolph |
| 6,787,682 B2 | 9/2004 | Gilman |
| 6,800,074 B2 | 10/2004 | Henley et al. |
| 6,808,517 B2 | 10/2004 | Greter et al. |
| 6,814,079 B2 | 11/2004 | Heaton et al. |
| 6,824,533 B2 | 11/2004 | Risk, Jr. et al. |
| 6,855,135 B2 | 2/2005 | Lockwood et al. |
| 6,856,821 B2 | 2/2005 | Johnson |
| 6,936,037 B2 | 8/2005 | Bubb |
| 6,951,553 B2 | 10/2005 | Bubb et al. |
| 6,960,179 B2 | 11/2005 | Gura |

(56) References Cited

U.S. PATENT DOCUMENTS

| | | |
|---|---|---|
| 6,977,323 B1 | 12/2005 | Swenson |
| 6,979,324 B2 | 12/2005 | Bybordi et al. |
| 6,987,209 B2 | 1/2006 | Augustine et al. |
| 6,994,702 B1 | 2/2006 | Johnson |
| 6,997,897 B1 | 2/2006 | Silver et al. |
| 7,004,915 B2 | 2/2006 | Boynton et al. |
| 7,008,400 B2 | 3/2006 | Silver et al. |
| 7,022,113 B2 | 4/2006 | Lockwood et al. |
| 7,067,709 B2 | 6/2006 | Murata et al. |
| 7,070,584 B2 | 7/2006 | Johnson et al. |
| 7,077,832 B2 | 7/2006 | Fleischmann |
| 7,087,806 B2 | 8/2006 | Scheinberg et al. |
| 7,108,683 B2 | 9/2006 | Zamierowski |
| 7,117,869 B2 | 10/2006 | Heaton et al. |
| 7,122,046 B2 | 10/2006 | Augustine et al. |
| 7,128,735 B2 | 10/2006 | Weston |
| 7,141,714 B2 | 11/2006 | Nielsen |
| 7,195,624 B2 | 3/2007 | Lockwood |
| 7,214,202 B1 | 5/2007 | Vogel et al. |
| 7,216,651 B2 | 5/2007 | Argenta et al. |
| 7,238,850 B2 | 7/2007 | Shimanuki |
| 7,255,681 B1 | 8/2007 | Silver et al. |
| 7,273,054 B2 | 9/2007 | Heaton et al. |
| 7,279,612 B1 | 10/2007 | Heaton et al. |
| 7,316,672 B1 | 1/2008 | Hunt et al. |
| 7,335,809 B2 | 2/2008 | Riesinger |
| 7,338,482 B2 | 3/2008 | Lockwood et al. |
| 7,361,184 B2 | 4/2008 | Joshi |
| 7,381,211 B2 | 6/2008 | Zamierowski |
| 7,381,859 B2 | 6/2008 | Hunt et al. |
| 7,438,705 B2 | 10/2008 | Karpowicz et al. |
| 7,470,830 B2 | 12/2008 | Sigurjonsson et al. |
| 7,485,112 B2 | 2/2009 | Karpowicz et al. |
| 7,494,482 B2 | 2/2009 | Orgill et al. |
| 7,503,910 B2 | 3/2009 | Adahan |
| 7,507,870 B2 | 3/2009 | Nielsen et al. |
| 7,524,286 B2 | 4/2009 | Johnson |
| 7,524,315 B2 | 4/2009 | Blott et al. |
| 7,534,240 B1 | 5/2009 | Johnson |
| 7,534,927 B2 | 5/2009 | Lockwood |
| 7,569,742 B2 | 8/2009 | Haggstrom et al. |
| 7,601,129 B2 | 10/2009 | Aali |
| 7,611,500 B1 | 11/2009 | Lina et al. |
| 7,612,247 B2 | 11/2009 | Oyaski |
| 7,615,036 B2 | 11/2009 | Joshi et al. |
| 7,625,362 B2 | 12/2009 | Boehringer |
| 7,645,269 B2 | 1/2010 | Zamierowski |
| 7,670,323 B2 | 3/2010 | Hunt et al. |
| 7,678,090 B2 | 3/2010 | Risk, Jr. |
| 7,699,823 B2 | 4/2010 | Haggstrom et al. |
| 7,699,830 B2 | 4/2010 | Martin |
| 7,700,819 B2 | 4/2010 | Ambrosio et al. |
| 7,708,724 B2 | 5/2010 | Weston |
| 7,717,313 B2 | 5/2010 | Criscuolo et al. |
| 7,722,582 B2 | 5/2010 | Lina et al. |
| 7,731,702 B2 | 6/2010 | Bybordi et al. |
| 7,745,681 B1 | 6/2010 | Ferguson |
| 7,753,894 B2 | 7/2010 | Blott et al. |
| 7,754,936 B2 | 7/2010 | Heaton et al. |
| 7,758,514 B2 | 7/2010 | Grigoryants et al. |
| 7,758,554 B2 | 7/2010 | Lina et al. |
| 7,759,537 B2 | 7/2010 | Bishop et al. |
| 7,759,538 B2 | 7/2010 | Fleischmann |
| 7,759,539 B2 | 7/2010 | Shaw et al. |
| 7,763,000 B2 | 7/2010 | Risk, Jr. et al. |
| 7,775,998 B2 | 8/2010 | Riesinger |
| 7,776,028 B2 | 8/2010 | Miller et al. |
| 7,779,625 B2 | 8/2010 | Joshi et al. |
| 7,790,945 B1 | 9/2010 | Watson, Jr. |
| 7,790,946 B2 | 9/2010 | Mulligan |
| 7,794,438 B2 | 9/2010 | Henley et al. |
| 7,794,450 B2 | 9/2010 | Blott et al. |
| 7,803,980 B2 | 9/2010 | Griffiths et al. |
| 7,811,269 B2 | 10/2010 | Boynton et al. |
| 7,815,616 B2 | 10/2010 | Boehringer et al. |
| 7,816,577 B2 | 10/2010 | Aali |
| 7,828,782 B2 | 11/2010 | Suzuki |
| 7,838,716 B2 | 11/2010 | de Luis et al. |
| 7,838,717 B2 | 11/2010 | Haggstrom et al. |
| 7,846,141 B2 | 12/2010 | Weston |
| 7,857,806 B2 | 12/2010 | Karpowicz et al. |
| 7,858,838 B2 | 12/2010 | Holm et al. |
| 7,862,339 B2 | 1/2011 | Mulligan |
| 7,867,206 B2 | 1/2011 | Lockwood et al. |
| 7,880,050 B2 | 2/2011 | Robinson et al. |
| 7,884,258 B2 | 2/2011 | Boehringer et al. |
| 7,886,746 B2 | 2/2011 | Heaton et al. |
| 7,896,823 B2 | 3/2011 | Mangrum et al. |
| 7,896,856 B2 | 3/2011 | Petrosenko et al. |
| 7,909,805 B2 | 3/2011 | Weston |
| 7,910,791 B2 | 3/2011 | Coffey |
| 7,922,703 B2 | 4/2011 | Riesinger |
| 7,927,318 B2 | 4/2011 | Risk, Jr. et al. |
| 7,931,630 B2 | 4/2011 | Nishtala et al. |
| 7,951,100 B2 | 5/2011 | Hunt et al. |
| 7,951,124 B2 | 5/2011 | Boehringer et al. |
| 7,959,624 B2 | 6/2011 | Riesinger |
| 7,964,766 B2 | 6/2011 | Blott et al. |
| 7,976,519 B2 | 7/2011 | Bubb et al. |
| D642,594 S | 8/2011 | Mattson et al. |
| 7,988,680 B2 | 8/2011 | Lockwood et al. |
| 7,998,125 B2 | 8/2011 | Weston |
| 8,007,257 B2 | 8/2011 | Heaton et al. |
| 8,021,348 B2 | 9/2011 | Risk, Jr. et al. |
| 8,022,266 B2 | 9/2011 | Boehringer et al. |
| 8,025,650 B2 | 9/2011 | Anderson et al. |
| 8,034,037 B2 | 10/2011 | Adams et al. |
| 8,062,272 B2 | 11/2011 | Weston |
| 8,062,273 B2 | 11/2011 | Weston |
| 8,080,702 B2 | 12/2011 | Blott et al. |
| 8,084,663 B2 | 12/2011 | Watson, Jr. |
| 8,092,441 B2 | 1/2012 | Sugito |
| 8,100,887 B2 | 1/2012 | Weston et al. |
| 8,105,295 B2 | 1/2012 | Blott et al. |
| 8,118,794 B2 | 2/2012 | Weston |
| 8,133,211 B2 | 3/2012 | Cavanaugh, II et al. |
| 8,152,785 B2 | 4/2012 | Vitaris |
| 8,158,844 B2 | 4/2012 | McNeil |
| 8,162,907 B2 | 4/2012 | Heagle |
| 8,162,909 B2 | 4/2012 | Blott et al. |
| 8,207,392 B2 | 6/2012 | Haggstrom et al. |
| 8,211,071 B2 | 7/2012 | Mormino et al. |
| 8,215,929 B2 | 7/2012 | Shen et al. |
| 8,235,955 B2 | 8/2012 | Blott et al. |
| 8,241,261 B2 | 8/2012 | Randolph et al. |
| 8,251,979 B2 | 8/2012 | Malhi |
| 8,257,327 B2 | 9/2012 | Blott et al. |
| 8,257,328 B2 | 9/2012 | Augustine et al. |
| 8,282,611 B2 | 10/2012 | Weston |
| 8,303,552 B2 | 11/2012 | Weston |
| 8,308,714 B2 | 11/2012 | Weston et al. |
| 8,323,264 B2 | 12/2012 | Weston et al. |
| 8,348,910 B2 | 1/2013 | Blott et al. |
| 8,382,731 B2 | 2/2013 | Johannison |
| 8,404,921 B2 | 3/2013 | Lee et al. |
| D679,819 S | 4/2013 | Peron |
| D679,820 S | 4/2013 | Peron |
| 8,494,349 B2 | 7/2013 | Gordon |
| 8,569,566 B2 | 10/2013 | Blott et al. |
| 8,715,256 B2 | 5/2014 | Greener |
| 8,795,244 B2 | 8/2014 | Randolph et al. |
| 8,808,274 B2 * | 8/2014 | Hartwell ..................... 604/543 |
| 2001/0029956 A1 | 10/2001 | Argenta |
| 2001/0031911 A1 | 10/2001 | Khouri |
| 2001/0034499 A1 | 10/2001 | Sessions et al. |
| 2001/0038799 A1 | 11/2001 | Silver et al. |
| 2001/0043943 A1 | 11/2001 | Coffey |
| 2002/0002209 A1 | 1/2002 | Mork |
| 2002/0017304 A1 | 2/2002 | Heaton et al. |
| 2002/0026133 A1 | 2/2002 | Augustine et al. |
| 2002/0082567 A1 | 6/2002 | Lockwood et al. |
| 2002/0143286 A1 | 10/2002 | Tumey |
| 2002/0161317 A1 | 10/2002 | Risk et al. |
| 2002/0161346 A1 | 10/2002 | Lockwood et al. |

(56) References Cited

U.S. PATENT DOCUMENTS

| | | |
|---|---|---|
| 2002/0183702 A1 | 12/2002 | Henley et al. |
| 2002/0198503 A1 | 12/2002 | Risk, Jr. et al. |
| 2002/0198504 A1 | 12/2002 | Risk et al. |
| 2003/0021775 A1 | 1/2003 | Freeman |
| 2003/0023286 A1 | 1/2003 | Augustine et al. |
| 2003/0040687 A1 | 2/2003 | Boynton et al. |
| 2003/0045825 A1 | 3/2003 | Etheredge, III |
| 2003/0050594 A1 | 3/2003 | Zamierowski |
| 2003/0069529 A1 | 4/2003 | Augustine et al. |
| 2003/0069536 A1 | 4/2003 | Greter et al. |
| 2003/0069563 A1 | 4/2003 | Johnson |
| 2003/0125649 A1 | 7/2003 | Mcintosh et al. |
| 2003/0144619 A1 | 7/2003 | Augustine |
| 2003/0171675 A1 | 9/2003 | Rosenberg |
| 2003/0175798 A1 | 9/2003 | Raees et al. |
| 2003/0188754 A1 | 10/2003 | Heaton et al. |
| 2003/0212357 A1 | 11/2003 | Pace |
| 2003/0212431 A1 | 11/2003 | Brady et al. |
| 2003/0219469 A1 | 11/2003 | Johnson et al. |
| 2003/0225347 A1 | 12/2003 | Argenta et al. |
| 2004/0006319 A1 | 1/2004 | Lina et al. |
| 2004/0019342 A1 | 1/2004 | Nagasuna et al. |
| 2004/0024351 A1 | 2/2004 | Greter et al. |
| 2004/0030304 A1 | 2/2004 | Hunt et al. |
| 2004/0039391 A1 | 2/2004 | Argenta et al. |
| 2004/0054338 A1 | 3/2004 | Bybordi et al. |
| 2004/0064111 A1 | 4/2004 | Lockwood et al. |
| 2004/0064132 A1 | 4/2004 | Boehringer et al. |
| 2004/0122434 A1 | 6/2004 | Argenta et al. |
| 2004/0127862 A1 | 7/2004 | Bubb et al. |
| 2004/0127863 A1 | 7/2004 | Bubb et al. |
| 2004/0167482 A1 | 8/2004 | Watson |
| 2004/0171976 A1 | 9/2004 | Johnson |
| 2004/0241214 A1 | 12/2004 | Kirkwood et al. |
| 2004/0249353 A1 | 12/2004 | Risks, Jr. et al. |
| 2005/0020955 A1 | 1/2005 | Sanders et al. |
| 2005/0085768 A1 | 4/2005 | Greter et al. |
| 2005/0090787 A1 | 4/2005 | Risk et al. |
| 2005/0131327 A1 | 6/2005 | Lockwood et al. |
| 2005/0165350 A1 | 7/2005 | Greter et al. |
| 2005/0177086 A1 | 8/2005 | Murata et al. |
| 2005/0228329 A1 | 10/2005 | Boehringer et al. |
| 2005/0245850 A1 | 11/2005 | Freyre et al. |
| 2005/0283105 A1 | 12/2005 | Heaton et al. |
| 2006/0009744 A1 | 1/2006 | Erdman et al. |
| 2006/0029650 A1 | 2/2006 | Coffey |
| 2006/0069365 A1 | 3/2006 | Sperl et al. |
| 2006/0070458 A1 | 4/2006 | Jones et al. |
| 2006/0079852 A1 | 4/2006 | Bubb et al. |
| 2006/0149170 A1 | 7/2006 | Boynton et al. |
| 2006/0282028 A1 | 12/2006 | Howard et al. |
| 2007/0005028 A1 | 1/2007 | Risk et al. |
| 2007/0021697 A1 | 1/2007 | Ginther et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0055209 A1 | 3/2007 | Patel et al. |
| 2007/0167927 A1 | 7/2007 | Hunt et al. |
| 2007/0185463 A1 | 8/2007 | Mulligan |
| 2007/0219513 A1 | 9/2007 | Lina et al. |
| 2007/0225663 A1 | 9/2007 | Watt et al. |
| 2007/0260207 A1 | 11/2007 | Ugander et al. |
| 2008/0009812 A1 | 1/2008 | Riesinger |
| 2008/0033352 A1 | 2/2008 | Annis et al. |
| 2008/0039761 A1 | 2/2008 | Heaton et al. |
| 2008/0045887 A1 | 2/2008 | Larsson et al. |
| 2008/0082059 A1 | 4/2008 | Fink et al. |
| 2008/0108977 A1 | 5/2008 | Heaton et al. |
| 2008/0167593 A1 | 7/2008 | Fleischmann |
| 2008/0177253 A1 | 7/2008 | Boehringer et al. |
| 2008/0200905 A1 | 8/2008 | Heaton |
| 2008/0208147 A1 | 8/2008 | Argenta et al. |
| 2008/0223378 A1 | 9/2008 | Henderson et al. |
| 2008/0234641 A1 | 9/2008 | Locke et al. |
| 2008/0243044 A1 | 10/2008 | Hunt et al. |
| 2008/0294147 A1 | 11/2008 | Radl et al. |
| 2008/0306407 A1 | 12/2008 | Taylor |
| 2008/0306456 A1 | 12/2008 | Riesinger |
| 2008/0312572 A1 | 12/2008 | Riesinger |
| 2008/0312613 A1 | 12/2008 | Heaton et al. |
| 2009/0005746 A1 | 1/2009 | Nielsen et al. |
| 2009/0036873 A1 | 2/2009 | Nielsen et al. |
| 2009/0054855 A1 | 2/2009 | Blott et al. |
| 2009/0082740 A1 | 3/2009 | Lockwood et al. |
| 2009/0093779 A1 | 4/2009 | Riesinger |
| 2009/0124988 A1 | 5/2009 | Coulthard |
| 2009/0131892 A1 | 5/2009 | Karpowicz et al. |
| 2009/0137973 A1 | 5/2009 | Karpowicz et al. |
| 2009/0192467 A1 | 7/2009 | Hansen et al. |
| 2009/0198201 A1 | 8/2009 | Adahan |
| 2009/0204085 A1 | 8/2009 | Biggie et al. |
| 2009/0216170 A1 | 8/2009 | Robinson et al. |
| 2009/0216204 A1 | 8/2009 | Bhavaraju et al. |
| 2009/0221977 A1 | 9/2009 | Blott et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0234309 A1 | 9/2009 | Vitaris et al. |
| 2009/0240185 A1 | 9/2009 | Jaeb et al. |
| 2009/0254053 A1 | 10/2009 | Svensby et al. |
| 2009/0254066 A1 | 10/2009 | Heaton |
| 2009/0259203 A1 | 10/2009 | Hu et al. |
| 2009/0264807 A1 | 10/2009 | Haggstrom et al. |
| 2009/0264837 A1 | 10/2009 | Adahan |
| 2009/0270820 A1 | 10/2009 | Johnson |
| 2009/0287129 A1 | 11/2009 | Boehringer et al. |
| 2009/0293887 A1 | 12/2009 | Wilkes et al. |
| 2009/0299251 A1 | 12/2009 | Buan |
| 2009/0299255 A1 | 12/2009 | Kazala, Jr. et al. |
| 2009/0306580 A1 | 12/2009 | Blott et al. |
| 2009/0312723 A1 | 12/2009 | Blott et al. |
| 2010/0004611 A1 | 1/2010 | Aali |
| 2010/0016767 A1 | 1/2010 | Jones et al. |
| 2010/0022972 A1 | 1/2010 | Lina et al. |
| 2010/0030170 A1 | 2/2010 | Keller et al. |
| 2010/0030171 A1 | 2/2010 | Canada et al. |
| 2010/0030178 A1 | 2/2010 | MacMeccan et al. |
| 2010/0036334 A1 | 2/2010 | Heagle et al. |
| 2010/0063483 A1 | 3/2010 | Adahan |
| 2010/0069858 A1 | 3/2010 | Olson |
| 2010/0069863 A1 | 3/2010 | Olson |
| 2010/0087767 A1 | 4/2010 | McNeil |
| 2010/0100063 A1 | 4/2010 | Joshi et al. |
| 2010/0106112 A1 | 4/2010 | Vogel |
| 2010/0106117 A1 | 4/2010 | Lockwood et al. |
| 2010/0121286 A1 | 5/2010 | Locke et al. |
| 2010/0122417 A1 | 5/2010 | Vrzalik et al. |
| 2010/0125258 A1 | 5/2010 | Coulthard et al. |
| 2010/0145289 A1 | 6/2010 | Lina et al. |
| 2010/0150991 A1 | 6/2010 | Bernstein |
| 2010/0159192 A1 | 6/2010 | Cotton |
| 2010/0160878 A1 | 6/2010 | Hunt et al. |
| 2010/0160880 A1 | 6/2010 | Weston |
| 2010/0174251 A1 | 7/2010 | Weston |
| 2010/0191196 A1 | 7/2010 | Heagle |
| 2010/0191198 A1 | 7/2010 | Heagle |
| 2010/0207768 A1 | 8/2010 | Pidgeon |
| 2010/0210986 A1 | 8/2010 | Sanders |
| 2010/0228205 A1 | 9/2010 | Hu et al. |
| 2010/0249733 A9 | 9/2010 | Blott |
| 2010/0262090 A1 | 10/2010 | Riesinger |
| 2010/0262091 A1 | 10/2010 | Larsson |
| 2010/0268198 A1 | 10/2010 | Buan et al. |
| 2010/0280468 A1 | 11/2010 | Haggstrom et al. |
| 2010/0305490 A1 | 12/2010 | Coulthard et al. |
| 2010/0305526 A1 | 12/2010 | Robinson et al. |
| 2010/0318043 A1 | 12/2010 | Malhi et al. |
| 2010/0324510 A1 | 12/2010 | Andresen et al. |
| 2010/0331797 A1 | 12/2010 | Patel et al. |
| 2011/0004172 A1 | 1/2011 | Eckstein et al. |
| 2011/0004173 A1 | 1/2011 | Hu et al. |
| 2011/0015593 A1 | 1/2011 | Svedman et al. |
| 2011/0022013 A1 | 1/2011 | Boynton et al. |
| 2011/0028290 A1 | 2/2011 | Ozawa |

(56) References Cited

U.S. PATENT DOCUMENTS

| | | |
|---|---|---|
| 2011/0028918 A1 | 2/2011 | Hartwell |
| 2011/0028919 A1 | 2/2011 | Johnnison et al. |
| 2011/0028920 A1 | 2/2011 | Johannison |
| 2011/0028921 A1 | 2/2011 | Hartwell et al. |
| 2011/0034869 A1 | 2/2011 | Greter et al. |
| 2011/0034888 A1 | 2/2011 | Aali |
| 2011/0034892 A1 | 2/2011 | Buan |
| 2011/0034894 A1 | 2/2011 | Riesinger |
| 2011/0054422 A1 | 3/2011 | Locke et al. |
| 2011/0054423 A1 | 3/2011 | Blott et al. |
| 2011/0092927 A1 | 4/2011 | Wilkes et al. |
| 2011/0092958 A1 | 4/2011 | Jacobs |
| 2011/0105963 A1 | 5/2011 | Hu et al. |
| 2011/0106030 A1 | 5/2011 | Scholz |
| 2011/0112492 A1 | 5/2011 | Bharti et al. |
| 2011/0118683 A1 | 5/2011 | Weston |
| 2011/0125066 A1 | 5/2011 | Robinson et al. |
| 2011/0130712 A1 | 6/2011 | Topaz |
| 2011/0172617 A1 | 7/2011 | Riesinger |
| 2011/0230849 A1 | 9/2011 | Coulthard |
| 2011/0270201 A1 | 11/2011 | Bubb et al. |
| 2011/0270202 A1 | 11/2011 | Boehringer et al. |
| 2011/0282309 A1 | 11/2011 | Adie et al. |
| 2011/0313373 A1 | 12/2011 | Riesinger |
| 2011/0313374 A1 | 12/2011 | Lockwood et al. |
| 2012/0041399 A1 | 2/2012 | Blott et al. |
| 2012/0095380 A1 | 4/2012 | Gergely et al. |
| 2012/0109085 A1 | 5/2012 | McNeil |
| 2012/0130332 A1 | 5/2012 | Cotton et al. |
| 2012/0136325 A1 | 5/2012 | Allen et al. |
| 2013/0110058 A1 | 5/2013 | Adie et al. |
| 2013/0150814 A1 | 6/2013 | Buan |
| 2013/0274688 A1 | 10/2013 | Weston |
| 2014/0018753 A1 | 1/2014 | Joshi et al. |
| 2014/0228791 A1 | 8/2014 | Hartwell |
| 2014/0236109 A1 | 8/2014 | Greener |
| 2014/0343519 A1 | 11/2014 | Weston |
| 2015/0224238 A1 | 8/2015 | Hartwell |

FOREIGN PATENT DOCUMENTS

| | | |
|---|---|---|
| DE | 3 032 092 | 8/1980 |
| DE | 3 137 839 | 3/1983 |
| DE | 3 935 818 | 5/1991 |
| DE | 4 012 232 | 10/1991 |
| DE | 198 44 355 | 4/2000 |
| EP | 0 020 662 | 7/1984 |
| EP | 0 355 186 | 2/1990 |
| EP | 0 619 105 | 10/1994 |
| EP | 0 777 504 | 10/1998 |
| EP | 1 013 290 | 6/2000 |
| EP | 1 411 874 | 7/2001 |
| EP | 1 726 276 | 11/2006 |
| EP | 1 923 077 | 11/2006 |
| EP | 1 880 840 | 1/2008 |
| EP | 1 985 270 | 10/2008 |
| EP | 1 121 163 | 11/2008 |
| EP | 2 185 206 | 1/2009 |
| EP | 2 178 573 | 2/2009 |
| EP | 2 098 257 | 9/2009 |
| EP | 1 985 270 | 12/2009 |
| EP | 2 326 295 | 3/2010 |
| EP | 2 335 749 | 6/2011 |
| EP | 2 349 155 | 8/2011 |
| EP | 1 263 366 | 9/2011 |
| EP | 2 420 214 | 2/2012 |
| FR | 1163907 | 10/1958 |
| GB | 114754 | 4/1918 |
| GB | 236350 | 7/1925 |
| GB | 641061 | 8/1950 |
| GB | 1224009 | 3/1971 |
| GB | 1400124 | 7/1975 |
| GB | 1549756 | 8/1979 |
| GB | 2195255 | 4/1988 |
| GB | 2307180 | 5/1997 |
| GB | 2378392 | 2/2003 |
| GB | 2415908 | 1/2006 |
| JP | 59-86824 | 6/1984 |
| JP | 59-87824 | 6/1984 |
| JP | S61-80018 | 5/1986 |
| JP | 2003-165843 | 6/2003 |
| JP | 2005-334188 | 12/2005 |
| SU | 1251912 A1 | 4/1983 |
| WO | WO 84/01904 | 5/1984 |
| WO | WO 90/11795 | 10/1990 |
| WO | WO 91/00718 | 1/1991 |
| WO | WO 92/20299 | 11/1992 |
| WO | WO 96/05873 | 2/1996 |
| WO | WO 99/01173 | 1/1999 |
| WO | WO 00/07653 | 2/2000 |
| WO | WO 00/50143 | 8/2000 |
| WO | WO 00/59424 | 10/2000 |
| WO | WO 01/19430 | 3/2001 |
| WO | WO 01/34223 | 5/2001 |
| WO | WO 01/37922 A2 | 5/2001 |
| WO | WO 01/37922 A3 | 5/2001 |
| WO | WO 01/85248 | 11/2001 |
| WO | WO 02/083046 | 10/2002 |
| WO | WO 02/092783 | 11/2002 |
| WO | WO 03/092620 | 11/2003 |
| WO | WO 2004/024300 | 3/2004 |
| WO | WO 2004/037334 | 5/2004 |
| WO | WO 2005/009488 | 2/2005 |
| WO | WO 2005/016179 | 2/2005 |
| WO | WO 2005/025666 | 3/2005 |
| WO | WO 2005/046761 | 5/2005 |
| WO | WO 2005/051461 | 6/2005 |
| WO | WO 2005/070480 | 8/2005 |
| WO | WO 2005/079718 | 9/2005 |
| WO | WO 2005/082435 | 9/2005 |
| WO | WO 2005/105180 | 11/2005 |
| WO | WO 2005/123170 | 12/2005 |
| WO | WO 2006/048246 | 5/2006 |
| WO | WO 2006/052745 | 5/2006 |
| WO | WO 2006/056294 | 6/2006 |
| WO | WO 2006/081403 | 8/2006 |
| WO | WO 2006/116992 | 11/2006 |
| WO | WO 2007/002835 | 1/2007 |
| WO | WO 2007/013064 | 2/2007 |
| WO | WO 2007/019038 | 2/2007 |
| WO | WO 2007/024230 | 3/2007 |
| WO | WO 2007/030598 | 3/2007 |
| WO | WO 2007/030601 | 3/2007 |
| WO | WO 2007/084792 | 7/2007 |
| WO | WO 2007/085396 | 8/2007 |
| WO | WO 2007/092405 | 8/2007 |
| WO | WO 2007/106592 | 9/2007 |
| WO | WO 2007/133618 | 11/2007 |
| WO | WO 2008/013896 | 1/2008 |
| WO | WO 2008/027449 | 3/2008 |
| WO | WO 2008/040020 | 4/2008 |
| WO | WO 2008/041926 | 4/2008 |
| WO | WO 2008/100437 | 8/2008 |
| WO | WO 2008/100440 | 8/2008 |
| WO | WO 2008/112304 | 9/2008 |
| WO | WO 2009/019227 | 2/2009 |
| WO | WO 2009/019229 | 2/2009 |
| WO | WO 2009/047524 | 4/2009 |
| WO | WO 2009/062327 | 5/2009 |
| WO | WO 2009/066105 | 5/2009 |
| WO | WO 2009/066106 | 5/2009 |
| WO | WO 2009/089390 | 7/2009 |
| WO | WO 2009/103031 | 8/2009 |
| WO | WO 2009/111657 | 9/2009 |
| WO | WO 2009/117635 | 9/2009 |
| WO | WO 2009/122989 | 10/2009 |
| WO | WO 2009/126833 | 10/2009 |
| WO | WO 2009/146441 | 12/2009 |
| WO | WO 2009/151380 | 12/2009 |
| WO | WO 2009/156709 | 12/2009 |
| WO | WO 2009/158124 | 12/2009 |
| WO | WO 2009/158130 | 12/2009 |
| WO | WO 2010/026251 | 3/2010 |

(56) References Cited

FOREIGN PATENT DOCUMENTS

| WO | WO 2010/051418 | 5/2010 |
| WO | WO 2010/072309 | 7/2010 |
| WO | WO 2010/072395 | 7/2010 |
| WO | WO 2010/120776 | 10/2010 |
| WO | WO 2010/141271 | 12/2010 |
| WO | WO 2010/147592 | 12/2010 |
| WO | WO 2011/019476 | 2/2011 |
| WO | WO 2011/023275 | 3/2011 |
| WO | WO 2012/022484 | 2/2012 |

OTHER PUBLICATIONS

US 6,306,115, 10/2001, Kelly et al. (withdrawn).
U.S. Appl. No. 14/254,807, Apr. 16, 2014, Greener.
U.S. Appl. No. 14/259,026, Apr. 22, 2014, Hartwell.
U.S. Appl. No. 14/446,688, Jul. 30, 2014, Weston.
Achterberg, V., Ph.D., Hydroactive dressings and serum proteins: an in vitro study, Journal of Wound Care, February, vol. 5, No. 2, 1996 (pp. 79-82).
Argenta, Louis C., et al., "Vacuum-Assisted Closure: A New Method for Wound Control and Treatment; Clinical Experience", Ann Plas Surg 1997;38:563-577 (Dec. 10, 1996).
Aubrey, D.A. et al., Treatment of the Perineal Wound after Proctectomy by Intermittent Irrigation, Arch. Surg., Oct. 1984, 119, 1141-1144.
Bagautdinov, N.A., "Variant of External Vacuum Aspiration in the Treatment of Purulent Diseases of Soft Tissues," in current Problems in Modern Clinical Surgery: Interdepartmental Collection, edited by V. Ye. Volkov et al. (Chuvashia State University, Cheboksary, USSR 1986) pp. 94-96 (with English translation).
Braglina, I.O., et al. "Russian Chemical Bulletin", Dec. 31, 1983.
Chariker, M.E., et al, "Effective Management of Incisional and Cutaneous Fistulae with Closed Suction Wound Drainage," Contemporary Surgery. Jun. 1989, pp. 59-63, vol. 34 USA.
Chintamani, et al., "Half versus full vacuum suction drainage after modified radical mastectomy for breast cancer—a prospective randomized clinical trial", Research Article (Jan. 27, 2005), 1-5.
Davydov, Y.A., et al., The Bacteriological & Cytological Assessment of Vacuum Therapy of Purulent Wounds, Vestnik Chirurgia 1988, October Edition 48-52 (in Russian with English translation). 1987.
Davydov, Yu A., et al., "Concepts for Clinical Biological Management of the Wound Process in the Treatment of Purulent Wounds Using Vacuum Therapy", The Kremlin Papers: Perspectives in Wound Care, Russian Journal: Vestnik Khirurgii, BlueSky Publishing, La Costa, California (2004), 15-17.
Davydov, Yu A., et al., "The Bacteriological and Cytological Assessment of Vacuum Therapy of Purulent Wounds", The Kremlin Papers: Perspectives in Wound Care, Russian Journal: Vestnik Khirurgii, BlueSky Publishing, La Costa, California (2004), 11-14.
Davydov, Yu A., et al., "Vacuum Therapy in the Treatment of Purulent Lactation Mastitis", The Kremlin Papers: Perspectives in Wound Care, Russian Journal: Vestnik Khirurgii, BlueSky Publishing, La Costa, California (2004), 5-7.
De Lange, M.Y. , et al., "Vacuum-Assisted Closure: Indications and Clinical Experience", Eur J Plast Surg (2000) 2;178-182 (Feb. 9, 2000).
Dilmaghani et al., "A Method for Closed Irrigation and Suction Therapy in Deep Wound Infections," Journal of Bone and Joint Surgery, 1969, vol. 51-A, No. 2, pp. 323-342.
Hartz, R.S., et al., Healing of the Perineal Wound, Arch. Surg., Apr. 1980, 115, 471-474.
Health Technology, Literature R., "Vacuum Assisted Closure Therapy for Wound Care", Health Technology Literature Review (Dec. 2004), 3-59.
Kalypto Medical, NPD 1000 Product Brochure (publication date unknown, believed to be Nov. 2010).
Kalypto Medical, NPD 1000 Negative Pressure Wound Care System, Clinician & Patient Instructions for Use (publication date unknown, believed to be Feb. 2010).
Khirugii, Vestnik, "A Collection of Published Studies Complementing the Research and Innovation of Wound Care", The Kremlin Papers, Perspectives in Wound Care, Russian Medical Journal, Vestnik Khirugii, Blue Sky Publishing (2004), 2-17.
Kostiuchenok, B. M., et al., "The Vacuum Effect in the Surgical Treatment of Purulent Wounds", The Kremlin Papers: Perspectives in Wound Care, Russian Journal: Vestnik Khirurgii, BlueSky Publishing, La Costa, California (2004), 3-4.
Morykwas, Michael J., et al., "Vacuum-Assisted Closure: A New Method for Wound Control and Treatment: Animal Studies and Basic Foundation", Ann Plast Surg 1997;38:553-562 (Dec. 10, 1996).
NURSING75, Wound Suction: Better Drainage with Fewer Problems, Nursing, vol. 5, No. 10, Oct. 1975, pp. 52-55.
Prevena™ Incision Management System, Patient Guide, pp. 1-2, Jan. 2010.
Prevena™ Incision Management System, Clinician Guide, pp. 1-9, Jan. 2010.
Solovev, V. A., et al., "The Method of Treatment of Immature External Fistulas in the Upper Gastrointestinal Tract—Guidelines" USSR Ministry of Health, S. M. Kirov Gorky State Medical Institute, 1987 (with English translation).
Solovev, V.A. "Treatment and Prevention of Suture Failures after Gastric Resection" (Dissertation Abstract) (S.M. Kirov Gorky State Medical Institute, Gorky USSR 1988).
Stewart, Joanne, Ph.D., World Wide Wounds—Next generation of products for wound management—2002 (13 pages).
Svedman, P., "Irrigation Treatment in Split-Thickness Skin Grafting of Intractable Leg Ulcers," Scand J. Plast. Reconst. Surg., 19:211-213, 1985.
Svedman, P., "Irrigation Treatment of Leg Ulcers," The Lancet, Sep. 1983, 532-34.
Svedman, P., A Dressing Allowing Continuous Treatment of a Biosurface, IRCS Med. Science: Biomed. Tech.; Clinic. Med.; Surg. and Transplantation, 1979, 7, p. 221.
Svedman, P., et al., "A Dressing System Providing Fluid Supply and Suction Drainage Used for Continuous or Intermittent irrigation," Annals of Plastic Surgery, vol. 17, No. 2, Aug. 1986, pp. 125-133.
Swift, et al, "Quorum Sensing in *Aeromonas hydrophila* and *Aeromonas salmoncida*: Identification of LuxRI Homologs AhyRI and AsaRI and Their Cognate N-Acylhomoserine Lactone Signal Molecules," J. Bacteriol., 179(17):5271-5281 (1997).
Teder and Svedman et al., "Continuous Wound Irrigation in the Pig," Journal of Investigative Surgery, 1990, vol. 3, pp. 399-407.
Tribble, David E. M.D., An Improved Sump Drain-Irrigation Device of Simple Construction, Archives of Surgery New York, pp. 511-13, 1972 vol. 105.
Usupov, Y. N., et al., "Active Wound Drainage", The Kremlin Papers: Perspectives in Wound Care, Russian Journal: Vestnik Khirurgii, BlueSky Publishing, La Costa, California (2004), 810.
Venturi, Mark L., "Mechanisms and Clinical Applications of the Vacuum-Assisted Closure (VAC) Device", Am J Clin Dermatol (2005) 693, 185-194.
Vijanto, J. and J. Raekallio, Local Hyperalimentation of Open Wounds, Br. J. surg., 1976, 63, 427-430.
Webb, New Techniques in Wound Management: Vacuum-Assisted Wound Closure, Journal of the American Academy of Orthopadic Surgeons, v. 10, No. 5, pp. 303-311, Sep. 2002.
Westaby, S., et al., "A Wound Irrigation Device", The Lancet, Sep. 2, 1978, pp. 503-504.
Wooding-Scott, Margaret, et al., "No Wound is Too Big for Resourceful Nurses," RN Dec. 1988, pp. 22-25 USA.
Wound Suction, Nursing, Oct. 1975, USA pp. 52-53.

* cited by examiner

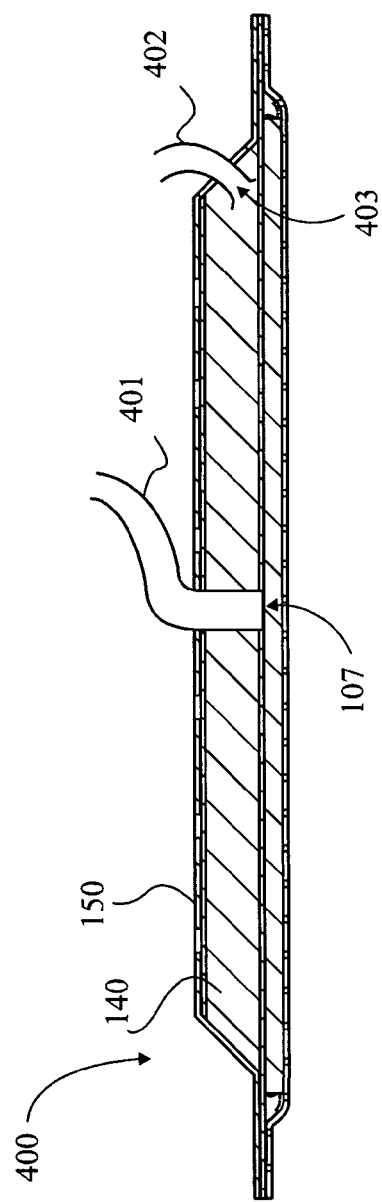

WOUND DRESSING

CROSS-REFERENCE TO RELATED APPLICATIONS

Any and all applications for which a foreign or domestic priority claim is identified in the Application Data Sheet as filed with the present application are hereby incorporated by reference under 37 CFR 1.57.

This application is a continuation of U.S. application Ser. No. 12/744,218, filed Sep. 20, 2010, which is the U.S. National Phase of PCT International Application No. PCT/GB2008/051089 filed on Nov. 20, 2008, designating the United States and published on May 28, 2009 as WO 2009/066105, which claims priority to Great Britain Patent Application No. 0722820.8, filed Nov. 21, 2007, and Great Britain Patent Application No. 0817040.9, filed Sep. 17, 2008. The disclosure of these prior applications are incorporated by reference in their entireties and should be considered a part of this specification.

BACKGROUND OF THE INVENTION

Field of the Invention

The present invention relates to a method and apparatus for dressing a wound and a method for manufacturing a wound dressing. In particular, but not exclusively, the present invention relates to a wound dressing useable during topical negative pressure (TNP) therapy in which the wound dressing itself acts as a waste canister to collect and store wound exudate removed from a wound site.

There is much prior art available relating to the provision of apparatus and methods of use thereof for the application of topical negative pressure (TNP) therapy to wounds together with other therapeutic processes intended to enhance the effects of the TNP therapy. Examples of such prior art include those listed and briefly described below.

TNP therapy assists in the closure and healing of wounds by reducing tissue oedema; encouraging blood flow and granulation of tissue; removing excess exudates and may reduce bacterial load and thus, infection to the wound. Furthermore, TNP therapy permits less outside disturbance of the wound and promotes more rapid healing.

In International patent application, WO 2004/037334, apparatus, a wound dressing and a method for aspirating, irrigating and cleansing wounds are described. In very general terms, the application describes the treatment of a wound by the application of TNP therapy for aspirating the wound together with the further provision of additional fluid for irrigating and/or cleansing the wound, which fluid, comprising both wound exudates and irrigation fluid, is then drawn off by the aspiration means and circulated through means for separating the beneficial materials therein from deleterious materials. The materials which are beneficial to wound healing are recirculated through the wound dressing and those materials deleterious to wound healing are discarded to a waste collection bag or vessel.

In International patent application, WO 2005/04670, apparatus, a wound dressing and a method for cleansing a wound using aspiration, irrigation and cleansing wounds are described. Again, in very general terms, the invention described in this document utilises similar apparatus to that in WO 2004/037334 with regard to the aspiration, irrigation and cleansing of the wound, however, it further includes the important additional step of providing heating means to control the temperature of that beneficial material being returned to the wound site/dressing so that it is at an optimum temperature, for example, to have the most efficacious therapeutic effect on the wound.

In International patent application, WO 2005/105180, apparatus and a method for the aspiration, irrigation and/or cleansing of wounds are described. Again, in very general terms, this document describes similar apparatus to the two previously mentioned documents hereinabove but with the additional step of providing means for the supply and application of physiologically active agents to the wound site/dressing to promote wound healing.

The content of the above-noted references is included herein by reference.

However, the above described apparatus and methods are generally only applicable to a patient when hospitalised as the apparatus used is complex, needing people having specialist knowledge in how to operate and maintain the apparatus, and also relatively heavy and bulky, not being adapted for easy mobility outside of a hospital environment by a patient, for example.

Some patients having relatively less severe wounds which do not require continuous hospitalisation, for example, but whom nevertheless would benefit from the prolonged application of TNP therapy, could be treated at home or at work subject to the availability of an easily portable and maintainable TNP therapy apparatus. To this end GB-A-2 307 180 describes a portable TNP therapy unit which may be carried by a patient and clipped to belt or harness. A negative pressure can thus be applied at a wound site.

During TNP therapy a portable or non-portable therapy unit generates a negative pressure at a wound site. As fluid, including air as well as wound exudate material is removed from the wound site this must be collected in some manner remote from the wound site. With prior known therapy units the collection and storage of wound exudate material is typically carried out by a waste canister connected to a pump unit of the therapy unit. The use of a canister, however, can result in the therapy unit apparatus itself being quite bulky and expensive to manufacture. Also replacing a canister or a bag in a canister in which wound exudate is collected can be a time consuming and relatively unhygienic process.

Prior known therapy units also tend to include a pump which is used to generate the negative pressure. Such pumps can be costly to manufacture and are relatively heavy.

WO 2007/030601, which is incorporated herein by reference discloses a self-contained wound dressing with a micro pump. The pump for drawing wound fluid into a vacuum zone is included in a wound dressing itself. Nevertheless wound exudate from the dressing can only be removed via a complex series of steps. The exudate removal process is also prone to contamination since once an absorbent layer is fully saturated with wound exudate an access door must be opened in the wound dressing so that the absorbent layer and micro pump can be removed. It will be appreciated that such exudate removal and pump removal can be time consuming and can lead to cross contamination between users. A further problem is that the wound dressing is prone to over expansion and rupture.

SUMMARY OF SOME EXEMPLIFYING EMBODIMENTS

It is an aim of the present invention to at least partly mitigate the above-mentioned problems.

It is an aim of certain embodiments of the present invention to provide a method for providing negative pressure at a wound site to aid in wound closure and healing in which wound exudate drawn from a wound site during the therapy is collected and stored in a wound dressing.

It is an aim of certain embodiments of the present invention to provide a wound dressing which is able to be placed over a wound site and which includes an integrated pump to generate negative pressure at that wound site. Also the wound dressing can collect any wound exudate.

According to a first aspect of the present invention there is provided apparatus for dressing a wound, comprising:
a sealing layer comprising at least one orifice;
an absorbent layer over the sealing layer for absorbing wound exudate; and
a liquid impermeable, gas permeable filter layer over the absorbent layer.

According to a second aspect of the present invention there is provided a method of applying topical negative pressure at a wound site, comprising the steps of:
via a pump element, pumping wound exudate and air from a wound site, a peripheral region around the wound site being sealed with a sealing layer of a wound dressing;
collecting wound exudate pumped from the wound site, through at least one orifice in the sealing layer, in an absorbent layer of the wound dressing; and
exhausting gas from the wound dressing through a filter layer between the absorbent layer and a cover layer extending over the wound dressing.

Certain embodiments of the present invention provide the advantage that a disposable wound dressing can be fixed over a wound site and can simultaneously be used to provide negative pressure at the wound site and collect and store wound exudate. A filter layer of the wound dressing permits air to be continually exhausted from the wound dressing as an integral pump or remote pump generates negative pressure at the wound site. This prevents a risk of over expansion.

Certain embodiments of the present invention provide the advantage that a separate therapy unit is not required to generate negative pressure at a wound site and collect and store any wound exudate. Rather a wound dressing can carry out both a pumping and wound exudate collecting process. The wound dressing may then be a one use item which can be disposed of subsequent to use. This reduces a risk of contamination.

Certain embodiments of the present invention provide the advantage that a wound dressing can be used to collect wound exudate generated during a negative pressure therapy process. A pump remote from the wound dressing can be connected to the wound dressing and reused whilst the wound dressing itself is used to collect wound exudate and may then be disposed of after use.

BRIEF DESCRIPTION OF THE DRAWINGS

Embodiments of the present invention will now be described hereinafter, by way of example only, with reference to the accompanying drawings in which:
FIG. 4 illustrates a wound dressing with an external pump.

DETAILED DESCRIPTION OF SOME EXEMPLIFYING EMBODIMENTS

Figure 1:
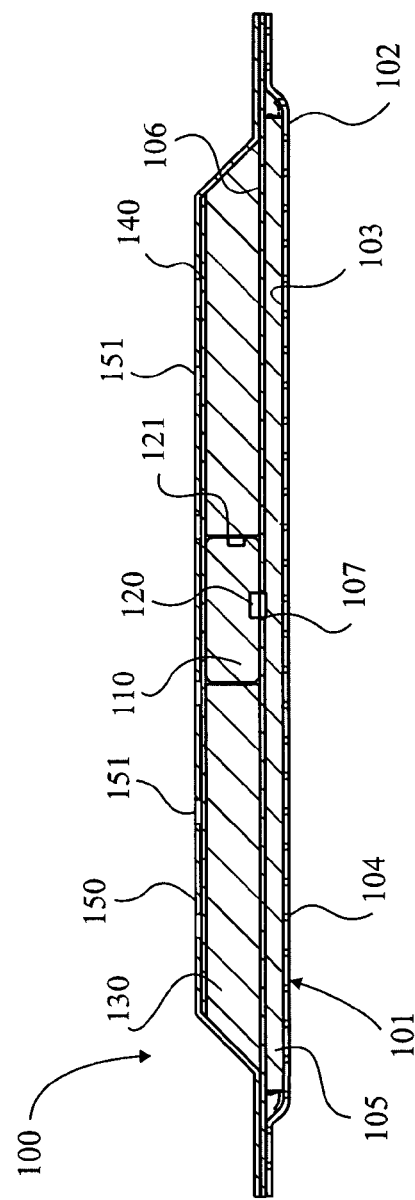
FIG. 1 illustrates a wound dressing.
Figure 2:
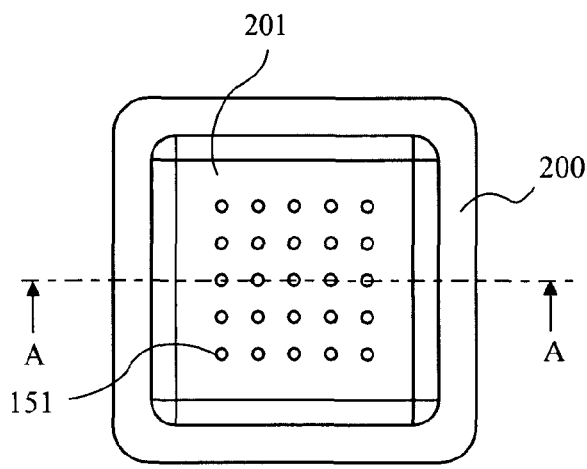
FIG. 2 illustrates a top view of a wound dressing.

In the drawings like reference numerals refer to like parts.
FIG. 1 illustrates a cross section through a wound dressing 100 according to an embodiment of the present invention. A plan view from above of the wound dressing 100 is illustrated in FIG. 2 with the line A-A indicating the location of the cross section shown in FIG. 1. It will be understood that FIG. 1 illustrates a generalised schematic view of an apparatus 100. It will be understood that embodiments of the present invention are generally applicable to use in topical negative pressure (TNP) systems. Briefly, negative pressure wound therapy assists in the closure and healing of many forms of "hard to heal" wounds by reducing tissue oedema; encouraging blood flow and granular tissue formation; removing excess exudate and reducing bacterial load (and thus infection risk). In addition, the therapy allows for less disturbance of a wound leading to more rapid healing.

The wound dressing 100 can be located over a wound site to be treated. The dressing 100 forms a sealed cavity over the wound site. Optionally wound packer material can be used within a wound cavity below the dressing. Aptly the packer material can be a gauze or reticulated PU foam material.

It is envisaged that the negative pressure range for the apparatus embodying the present invention may be between about −50 mmHg and −200 mmHg (note that these pressures are relative to normal ambient atmospheric pressure thus, −200 mmHg would be about 560 mmHg in practical terms). Aptly the pressure range may be between about −75 mmHg and −150 mmHg. Alternatively a pressure range of up to −75 mmHg, up to −80 mmHg or over −80 mmHg can be used. Also aptly a pressure range of below −75 mmHg could be used. Alternatively a pressure range of over −100 mmHg could be used or over −150 mmHg.

As illustrated in FIG. 1 a lower surface 101 of the wound dressing 100 is provided by an optional wound contact layer 102. The wound contact layer 102 can be a polyurethane layer or polyethylene layer or other flexible layer which is perforated, for example via a hot pin process or in some other way, or otherwise made permeable to liquid and gas. The wound contact layer has a lower surface 101 and an upper surface 103. The perforations 104 are through holes in the wound contact layer which enables fluid to flow through the layer. The wound contact layer helps prevent tissue ingrowth into the other material of the wound dressing. The perforations are small enough to meet this requirement but still allow fluid through. The wound contact layer also helps hold the whole wound dressing together and acts as a carrier for an optional lower and upper adhesive layer (not shown). For example, a lower pressure sensitive adhesive may be provided on the underside surface 101 of the wound dressing whilst an upper pressure sensitive adhesive layer may be provided on the upper surface 103 of the wound contact layer. The pressure sensitive adhesive which may be a silicone or acrylic based adhesive or other such adhesives may be formed on both sides or optionally on a selected one or none of the sides of the wound contact layer. When a lower pressure sensitive adhesive layer is utilised this helps adhere the wound dressing to the skin around a wound site.

A layer 105 of porous material such as a foam layer or the like is located above the wound contact layer. This porous layer allows transmission of fluid including liquid and gas away from a wound site into upper layers of the wound dressing. The layer 105 also helps distribute pressure generated by a pump, mentioned in more detail below, so that a whole wound site sees an equalised negative pressure. Reticulated foam or a non-woven material which might be natural or synthetic can be used as the porous material of the porous layer 105.

A gas impermeable sealing layer 106 extends across the width of the wound dressing. The sealing layer which may, for example, be a polyurethane film having a pressure sensitive adhesive on both sides is impermeable to gas and this layer thus operates to seal a wound cavity over which the wound dressing is placed. In this way an effective chamber is made beneath the sealing layer and between the sealing layer and a wound site where a negative pressure can be established. Aptly whilst the sealing layer is gas impermeable the material of the sealing layer can have a high moisture vapour permeability. For example Elastollan (Trade name) SP9109 manufactured by BASF. A dotted pattern spread acrylic adhesive can optionally be used to help improve moisture vapour permeability. An advantage of using a high moisture vapour permeability material as the sealing layer 160 is that the fluid handling capacity of the dressing may be increased significantly by the action of moisture transpiring through the film and dispersing into the atmosphere. Advantageously, transpiration rates can be easily achieved of the order of 3000 grams/centimeter square/24 hours as a result of the high humidity achieved in the dressing and intimate contact of material achieved during use of the apparatus at a negative pressure of up to 250 mmHg below atmospheric pressure.

As illustrated in FIG. 1 a single central orifice is provided in the sealing layer. It will be appreciated that as an alternative the single orifice 107 may be provided as a plurality of through holes. The orifice 107 enables a micro pump 1 10 with associated valves not shown, which is integral to the wound dressing, to suck fluid from a region beneath the sealing layer 106 into a region above the sealing layer 106. A pump inlet is located in a facing relationship to the orifice 107 whilst an outlet 121 of the pump 1 10 is arranged to exhaust fluid pumped through the pump into a layer 130 of absorbent material. The absorbent material which may be a foam or non-woven natural or synthetic material and which may optionally include or be super-absorbent material forms a reservoir for fluid, particularly liquid, removed from the wound site. The material of the absorbent layer also prevents liquid collected in the wound dressing from flowing in a sloshing manner. The absorbent layer 130 also helps distribute fluid throughout the layer via a wicking action so that fluid is drawn from a region proximate to the exhaust outlet 121 of the pump into more remote regions so that agglomeration near the pump exit is avoided.

A filter layer 140 is provided over the absorbent layer 130. A suitable material for the filter material of the filter layer 140 is 0.2 micron Gore™ expanded PTFE from the MMT range. Larger pore sizes can also be used but these may require a secondary filter layer to ensure full bioburden containment. As wound fluid contains lipids it is preferable, though not essential, to use an oleophobic filter membrane for example 1.0 micron MMT-332 prior to 0.2 micron MMT-323. This prevents the lipids from blocking the hydrophobic filter.

It will be understood that other types of material could be used for the filter layer. More generally a microporous membrane can be used which is a thin, flat sheet of polymeric material, this contains billions of microscopic pores. Depending upon the membrane chosen these pores can range in size from 0.01 to more than 10 micrometers. Microporous membranes are available in both hydrophilic (water filtering) and hydrophobic (water repellent) forms. Aptly the wound dressing 100 according to certain embodiments of the present invention uses microporous hydrophobic membranes (MHMs). Numerous polymers may be employed to form MHMs. For example, PTFE, polypropylene, PVDF and acrylic copolymer. All of these optional polymers can be treated in order to obtain specific surface characteristics that can be both hydrophobic and oleophobic. As such these will repel liquids with low surface tensions such as multi-vitamin infusions, lipids, surfactants, oils and organic solvents.

MHMs block liquids whilst allowing air to flow through the membranes. They are also highly efficient air filters eliminating potentially infectious aerosols and particles. A single piece of MHM is well known as an option to replace mechanical valves or vents. Incorporation of MHMs can thus reduce product assembly costs improving profits and costs/benefit ratio to a patient.

The filter layer 140 thus enables gas to be exhausted upwards through the wound dressing. Liquid, particulates and pathogens, however, are contained in the dressing.

A cover layer 150 covers the absorbent layer of the wound dressing 100. The cover layer which, for example, may be a polyurethane film acts as a bacterial barrier and helps hold in liquid to stop fouling. The cover layer is sealed to the filter layer. For example via adhesive or welding techniques. Gas leaving the dressing thus passes through the filter layer and then the holes 151 in the cover layer. The cover layer also provides integrity for the dressing and is permeable to moisture vapour and gas by virtue of through holes 151 provided in the cover layer, for example by way of an array of perforations. These help improve the permeability to moisture vapour and gas through the wound dressing. In an alternative embodiment the filter layer 140 may instead cover the whole dressing sealing with the sealing layer 106. A protector layer or reinforcing layer may be included (this may be a non-woven or perforated film). Aptly the cover layer 150 is made from a material having a high moisture vapour permeability. For example Elastollan (Trade name) SP9109 manufactured by BASF. A dotted pattern spread acrylic adhesive can optionally be used to help improve moisture vapour permeability. An advantage of using a high moisture vapour permeability material as the cover layer 160 is that the fluid handling capacity of the dressing may be increased significantly by the action of moisture transpiring through the film and dispersing into the atmosphere. Advantageously, transpiration rates can be easily achieved of the order of 3000 grams/centimeter square/24 hours as a result of the high humidity achieved in the dressing and intimate contact of material achieved during use of the apparatus at a negative pressure of up to 250 mmHg below atmospheric pressure.

Turning to FIG. 2 which illustrates a wound dressing 100 in accordance with an embodiment of the present invention one can see an upper surface of the cover layer 150 which extends radially outwardly away from a centre of the dressing into a border region 200 surrounding a central raised region 201 overlying the absorbent layer 130. FIG. 2 also helps illustrate the array of perforations 151 formed in the cover layer.

Figure 3:
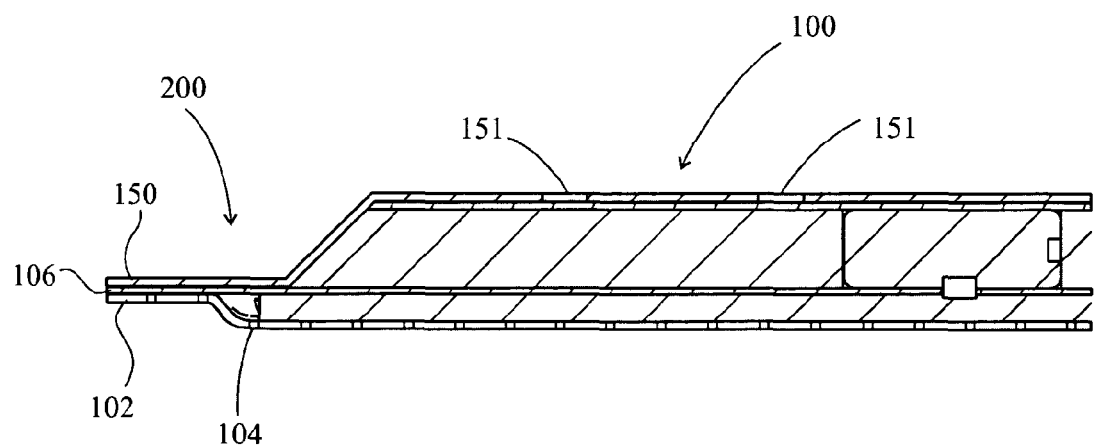
FIG. 3 illustrates a portion of the wound dressing.

FIG. 3 illustrates an expanded view of the border region 200 of the wound dressing 100 illustrated in FIGS. 1 and 2. As seen, the cover layer 150 extends over the absorbent layer 130 into an edge region. Here the cover layer is secured to the sealing layer 106 and the wound contact layer 102. FIG. 3 also helps illustrate how the perforations 104 in the wound contact layer 102 extend around the foam layer 105.

It will be understood that according to embodiments of the present invention the wound contact layer is optional. This layer is, if used, porous to water and faces an underlying wound site. A lower porous layer 105 such as a reticulated PU foam layer is used to distribute gas and fluid removal such that all areas of a wound are subjected to equal pressure. The sealing layer forms a substantially airtight seal over the wound. Thus as the pump 1 10 pumps a negative pressure is generated below the sealing layer. This negative pressure is thus experienced at the target wound site. Fluid including air and wound exudate is drawn through the wound contact layer and reticulated foam layer through the orifice 107 and into a fluid inlet 120 at the pump 1 10. The pump exhausts the fluid through a fluid exit 121 where the liquid component is wicked away so as to be collected and stored throughout the absorbent layer 130. The gaseous components of the exhausted fluid, together with some moisture vapour, are exhausted through the filter layer and through the perforations of the cover layer. The filter layer ensures that pathogens and unpleasant odours do not leave the reservoir region formed by the absorbent layer.

It will be appreciated by those skilled in the art that rather than have a cover layer overlying the filter layer the cover layer may itself be overlain by a filter layer. The cover layer may thus be the outermost layer of the wound dressing or the filter layer may be the outermost layer of the wound dressing. Further outer layers (not shown) may optionally be used so long as they are gas and water vapour permeable.

As still further options the dressing can contain anti-microbial e.g. nanocrystalline silver agents on the wound contact layer and/or silver sulphur diazine in the absorbent layer. These may be used separately or together. These respectively kill micro-organisms in the wound and micro-organisms in the absorption matrix. As a still further option other active components, for example, pain suppressants, such as ibuprofen, may be included. Also agents which enhance cell activity, such as growth factors or that inhibit enzymes, such as matrix metalloproteinase inhibitors, such as tissue inhibitors of metalloproteinase (TIMPS) or zinc chelators could be utilised. As a still further option odour trapping elements such as activated carbon, cyclodextrine, zealite or the like may be included in the absorbent layer or as a still further layer above the filter layer.

FIG. 4 illustrates an alternative embodiment of the present invention in which a pump is not provided integral within a wound dressing 400. Rather a connecting tube 401 is connected to an orifice 107 in the sealing layer. The outlet tube 401 is sealed around its outer circumference to the cover layer 150 and filter layer 140. The outlet conduit 401 is connected to a remote pump which may be some distance from the wound dressing 400 or may be mounted to a border of the wound dressing. An outlet of the remote pump is secured to an inlet tube 402 which is sealed about its circumference to a cover layer 150 leading to an opening 403. In this way as a pump is operated to apply a negative pressure to a zone below the sealing layer 106 exudate is drawn through the wound contact layer 102 and lower fluid distribution layer 105 through the orifice 107 and along the exit tube 401. Fluid, including air and wound exudate, passes through the pump and is exhausted in a region proximate to the opening 403 in outlet tube 402. The liquid part of the fluid is wicked away to be collected in the body of the absorbent layer 130. Air and moisture vapour passes through the filter layer and through the apertures in the cover layer into the ambient atmosphere.

It will be understood that according to embodiments of the present invention as fluid is drawn from a wound site the absorbent layer may expand. This may result in a slight bulge appearing in the upper surface of the filter and cover layer. In many respects the bulge can be used as a visible cue to indicate when a wound dressing should be replaced.

As mentioned above with respect to the embodiment shown in FIG. 4 a remote pump may be mounted to a border of the wound dressing in which case the tubes 401, 402 may be connected directly to the pump. Subsequent to a single use the wound dressing and pump may thus be discarded. As an option the tubes may be provided with a click fit connector or other easy fit connector which can be connected to corresponding mating connectors joined via corresponding tubes to a remote pump. In this way a remote pump may be reused whilst the wound dressing itself including connecting tubes and connectors is disposable after a single use.

It will be understood that for embodiments of the present invention which include a pump mounted on the cover layer or on a peripheral border area of the dressing an integral power source and control circuitry can be included. Alternatively the power source can be external to the pump and remotely mounted. A remote power source and/or control circuitry improves the disposability of the dressing and permits battery recharge if spare batteries are used.

It will also be appreciated that in use the dressing may be used "up-side down", at an angle or vertical. References to upper and lower are thus used for explanation purposes only.

It will be appreciated that alternatively the tubes 401, 402 could be a single dual lumen tube. As a still further alternative the tubes 401, 402 could alternatively be a single continuous looped tube, the tube then passing through pinch rollers for a peristaltic pump.

Throughout the description and claims of this specification, the words "comprise" and "contain" and variations of the words, for example "comprising" and "comprises", means "including but not limited to", and is not intended to (and does not) exclude other moieties, additives, components, integers or steps.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

What is claimed is:

1. A negative pressure apparatus to generate negative pressure at a wound site, comprising:
    a wound dressing comprising an adhesive to adhere the wound dressing to skin around a wound site, the wound dressing having a border region;
    a lower chamber surrounded by the border region and having a wound contact layer;
    an upper chamber separated from the lower chamber by a sealing layer formed of gas impermeable material, the upper chamber comprising at least one hole into the chamber and a gas permeable and liquid impermeable filter positioned to prevent the passage of fluids from the upper chamber through the at least one hole so that fluids drawn from the lower chamber are stored in the upper chamber; and
    a pump inlet in flow communication with the lower chamber, the pump inlet being operably connected with a negative pressure pump to apply negative pressure to the lower chamber to suck fluids therefrom and deliver the sucked fluids into the upper chamber, wherein the pump is integral within the wound dressing.

2. The apparatus of claim 1, wherein the sealing layer comprises a single orifice.

3. The apparatus of claim 1, wherein the sealing layer comprises a plurality of through holes.

4. The apparatus of claim 1, wherein the upper chamber comprises a cover layer comprising the at least one hole.

5. The apparatus of claim 1, wherein the at least one hole is configured to vent air from the upper chamber.

6. The apparatus of claim 1, wherein the lower chamber further comprises a porous layer configured to allow transmission of fluid away from the wound site and distribute negative pressure over at least a portion of the wound contact layer.

7. The apparatus of claim 1, wherein the upper chamber comprises an absorbent material configured to form a reservoir for fluid removed from the wound site.

8. The apparatus of claim 7, wherein the upper chamber comprises a cover layer configured to cover the absorbent material, wherein the cover layer comprises an edge region extending around a perimeter of the cover layer that surrounds the absorbent material.

9. The apparatus of claim 1, wherein the sealing layer comprises an edge region extending around a perimeter of the sealing layer that surrounds the lower chamber, the sealing layer configured to form a substantially air-tight seal over the wound site.

10. A negative pressure apparatus to generate negative pressure at a wound site, comprising:
- a wound dressing comprising an adhesive to adhere the wound dressing to skin around a wound site, the wound dressing comprising:
  - a lower chamber defined between a wound contact layer and a gas impermeable sealing layer;
  - an upper chamber separated from the lower chamber by the gas impermeable sealing layer, the upper chamber defined between the gas impermeable sealing layer and a cover layer;
  - one or more holes into the upper chamber to exhaust air from the upper chamber; and
  - a filter positioned to prevent the passage of liquid from the upper chamber;
- a pump inlet in fluid communication with the lower chamber, the pump inlet being operable to apply negative pressure to the lower chamber so that fluids drawn through the pump inlet are delivered into the upper chamber for storage therein; and
- a pump connected to the pump inlet to apply negative pressure to the lower chamber, the pump configured to extract fluids from the lower chamber and discharge the fluids into the upper chamber.

11. The apparatus of claim 10, wherein the wound dressing comprises a border region that surrounds the lower chamber.

12. The apparatus of claim 10, wherein the one or more holes are provided in the cover layer.

13. The apparatus of claim 10, wherein the sealing layer comprises one or more holes.

14. The apparatus of claim 10, wherein the pump is positioned within the wound dressing.

15. The apparatus of claim 14, wherein the pump is positioned within the upper chamber.

16. The apparatus of claim 10, further comprising an absorbent material within the upper chamber configured to collect and store wound exudate.

17. The apparatus of claim 10, wherein the filter is positioned at the one or more holes to permit passage of gas through the holes and prevent the passage of liquid from the upper chamber.

18. Apparatus for dressing a wound for topical negative pressure therapy, comprising:
- a wound contact layer;
- a porous layer arranged on the wound contact layer;
- a gas impermeable sealing layer arranged on the porous layer and comprising at least one orifice;
- an absorbent layer over the sealing layer for absorbing wound exudate;
- a liquid impermeable, gas permeable filter layer over the absorbent layer, wherein the filter layer is between the absorbent layer and an overlying cover layer; and
- a pump element, located between the cover layer and the sealing layer, comprising an inlet in fluid communication with the sealing layer orifice and an outlet in fluid communication with the absorbent layer.

19. The apparatus as claimed in claim 18, further comprising an adhesive layer on an upper and/or lower side of the wound contact layer.

20. The apparatus as claimed in claim 18, wherein the wound contact layer is sealed together with the sealing layer and cover layer in a border region.

* * * * *